United States Patent [19]

Schreuder

[11] Patent Number: 4,792,329

[45] Date of Patent: Dec. 20, 1988

[54] MULTI-COMPARTMENT SYRINGE

[75] Inventor: Johan C. Schreuder, Amsterdam, Netherlands

[73] Assignee: Duphar International Research B.V., Weesp, Netherlands

[21] Appl. No.: 877,734

[22] Filed: Jun. 24, 1986

[30] Foreign Application Priority Data

Jun. 27, 1985 [NL] Netherlands .................. 8501847

[51] Int. Cl.$^4$ .............................................. A61M 5/00
[52] U.S. Cl. ...................................... 604/90; 604/191
[58] Field of Search .................. 604/89, 90, 187, 191, 604/218, 222

[56] References Cited

U.S. PATENT DOCUMENTS

| | | | |
|---|---|---|---|
| 2,717,601 | 9/1955 | Brown | 604/90 X |
| 3,330,282 | 7/1967 | Visser et al. | 604/90 |
| 4,496,344 | 1/1985 | Kamstra | 604/191 X |
| 4,613,326 | 9/1986 | Szwarc | 604/89 |

Primary Examiner—Stephen C. Pellegrino
Attorney, Agent, or Firm—Stevens, Davis, Miller & Mosher

[57] ABSTRACT

The invention relates to a multi-compartment syringe comprising an ampoule having a plunger, a sealing stopper and at least one separating stopper between the plunger and the sealing stopper, and a needle holder consisting of a collar, a neck for an injection needle, a shaft between the collar and the neck and a by-pass means in the inner wall of the shaft, the space in the shaft of the needle holder being at least slightly longer than the sealing stopper, the ampoule wall comprising a liquid by-pass means through which the liquid behind the separating stopper or stoppers can reach the substance in front of the separating stopper or front separating stopper and can mix with same or can dissolve it, the ampoule, before use of the syringe, comprising an empty space in front of the sealing stopper.

14 Claims, 3 Drawing Sheets

MULTI-COMPARTMENT SYRINGE

The invention relates to a multi-compartment syringe in which two or more different substances which may not be in contact with each other for a longer period of time, can be stored separately before use, comprising

- a hollow, substantially cylindrical ampoule which is open at both ends,
- a plunger to which a plunger rod is or can be connected and which is movable in the ampoule and seals same,
- a sealing stopper which is entirely or substantially rotationally-symmetrical and the dimensions of which are such that the stopper can be provided in a sealing manner and so as to be movable in the ampoule in order to be able to separate the foremost substance provided or to be provided in the ampoule from the front end of the ampoule,
- at least one rotationally symmetrical separating stopper provided or to be provided in the ampoule between plunger and sealing stopper and being movable therein, the circumference of said stopper before use of the syringe adjoining the inner wall of the ampoule in a sealing manner and keeping the different substances present in the ampoule separated from each other,
- a finger grip or means for the connection thereof to the outside of the ampoule, and
- a needle holder comprising
   (a) a collar connected to the front end of the ampoule in a sealing manner,
   (b) a neck in which or to which a needle, optionally covered by a needle guard to keep the needle in a sterile condition, is or can be connected in a sealing manner.
   (c) a hollow, substantially cylindrical shaft between collar and neck, the shaft being proportioned so that the space bounded by the inner wall of the shaft and the rear face of the neck has the same or a slightly larger circumference than the inner wall of the ampoule and is at least longer than the sealing stopper, and
   (d) a by-pass means in the inner wall of the shaft through which the injection liquid behind the sealing stopper can reach the injection needle, when during use of the syringe, the sealing stopper is moved forward into the shaft of the needle holder.

Such a syringe, intended for the sequential injection of two or more different injection liquids which may not be in contact with each other for a longer period of time, is known from U.S. Pat. Nos. 4,439,184 and 4,496,344. The ampoule and the needle holder in the syringe from the first-mentioned U.S. patent specification are manufactured from one assembly so that there is no question of a separate needle holder. Such syringes as described in the above-mentioned U.S. patent specifications are intended more in particular for transport and storage while being filled with injection liquids, and to be used only once, so-called pre-fillable or pre-filled syringes.

In practice, these syringes have proved to give good satisfaction for sequentially injecting two or more injection liquids which are not compatible with each other for a longer period of time. However, it is often considered as a disadvantage that the various injection liquids are injected in the circulation system of the blood successively and are allowed to mix to some extent only further on in the body. For most injection liquids which are not compatible with each other a pre-mixing, i.e. a mixing immediately before the injection takes place, is not objectionable because undesired interactions or stability problems occur only in the long run. In some cases a pre-mixing is even necessary, namely when one of the injection liquids is not suitable for intravenous administration. This may be the case with an undiluted liquid medicament, or a medicament dissolved or mixed in a comparatively high concentration, in which the medicament must be diluted before the intravenous injection to obtain an acceptable injection liquid. When the undiluted or concentrated medicament is stable indeed, but the composition diluted to form an injection liquid is not stable, it is necessary to postpone the dilution until immediately before the injection. For such a purpose, a useful pre-filled or pre-fillable syringe has so far not been available.

It is the object of the present invention to provide a multi-compartment syringe with such a pre-mixing facility having the advantages known from the above-mentioned U.S. Pat. No. 4,496,344, such as a small dead space for injection liquid, a low resistance upon injection, a comparatively thick sealing stopper so that little diffusion will occur, a comparatively small number of simple components so that the cost of manufacture can be kept low, and the avoidance of piercing rubber components, in which so-called "particulate matter" can enter the injection liquid.

This object can be achieved by means of a syringe of the type mentioned in the opening paragraph which is characterized according to the invention in that:

- a liquid by-pass means is formed in the wall of the ampoule, which by-pass means has at least the same length as the separating stopper or the collective separating stoppers, and through which by-pass means, during use of the syringe, the liquid behind the separating stopper or stoppers can reach the substance in front of the separating stopper or front separating stopper and can mix with said substance or can dissolve it, but which by-pass means, before use of the syringe, is sealed from the liquid present behind said stopper by means of the separating stopper or front separating stopper, and
- the ampoule before use of the syringe comprises a space which is not filled with substance and which is bounded on the rear and lateral sides by the front face of the sealing stopper and the inner wall of the ampoule, and which on its front is in open communication with the space in the shaft of the needle holder, said empty space in the ampoule being at least as long as the distance from the front face of the piston to the rear end of said liquid by-pass means.

U.S. Pat. Nos. 2,549,417 and 2,717,601 disclose ampoules for syringes having a by-pass means for liquid in the form of a pair of ridges or grooves extending in the longitudinal direction. However, these ampoules are intended for use in a two-chamber syringe of the so-called wet-dry type, which means that the dry medicament is accommodated in the front compartment and the solvent for this medicament is accommodated in the rear compartment. In order to admit to the needle the injection liquid obtained after dissolving, the ampoule comprises at its front end a stopper which can be pierced by the sharp rear end of the injection needle, a by-pass for the liquid being formed. It will be obvious that such a construction has great disadvantages in practice because it is substantially inevitable that rubber particles ("particulate matter") will reach the injection liquid and can thus be also injected or can obstruct the injection needle. Moreover, the syringes described in the said U.S. patent specifications are not suitable for the object of the syringe according to the invention described hereinbefore, namely accomodating two or more injection liquids. When the front compartment would be filled with liquid, the stopper provided in the front end of the ampoule would be pushed out of the ampoule when the syringe is used. If it were considered to fill the front compartment only partly with liquid so as to permit a movement of the central stopper, then undesired pressure build-up will nevertheless occur in the front compartment during use, with the disadvantage to be described hereinafter; in addition, in that case the liquid in the front compartment would be in contact with a large amount of air for a long period of time, which in the case of oxidation-sensitive substances will lead to undesired oxidative conversions. Also when used for a solid medicament and a solvent therefor, the possibility is not excluded that during use, i.e. when moving the central stopper forward until the by-pass means for the solvent has been uncovered, the stopper will be pushed out of the front end of the ampoule by pressure build-up in the chamber in which the medicament is accommodated, as a result of which the syringe becomes useless for the purpose described. This pressure build-up has the additional disadvantage that a considerably greater force has to be exerted on the plunger rod for making the syringe operate. Moreover, it will be necessary for the glass wall of the ampoule to be able to withstand higher pressure so that a thicker glass wall is required.

As indicated hereinbefore, this problem has been solved in a simple manner in the syringe according to the invention by ensuring that an empty space is present in front of the sealing stopper, in which the sealing stopper can move forward when the syringe is used. The presence of this nonfilled space in front of the sealing stopper is characteristic of the present invention. The air present in said space can escape freely via the injection needle when the needle guard has previously been removed or when a needle guard with bacteria filter is used. This latter provision is of great advantage, because by using such a guard even during the mixing operation the contents of the syringe remain sterile. By situating the empty space, necessary for the pre-mixing operation of the syringe, in front of the sealing stopper, it can easily be ensured when filling the syringe that the liquid compartments comprise very little air, so that the possibility of undesired oxidative conversions when using oxidation-sensitive medicaments is considerably reduced.

In European patent application 144,551 a two-compartment medication syringe assembly is disclosed which in particular is intended for accomodating a solid medicament and a solvent for this medicament. Although in this syringe an empty space is present in front of the separating stopper to allow foreward movement of this stopper and subsequent solvent supply via the by-pass to the solid medicament, this syringe has serious draw-backs. To allow said foreward movement of the stopper and subsequent solvent supply without pressure build-up in the compartment accomodating the solid medicament, the cap closing the syringe tip or the needle shield should be removed beforehand. This means, that during the dissolving operation the content of the syringe, i.c. the solution to be injected, is in open communication with the environment, so that its sterility will be lost. A further practical disadvantage of this known syringe is that after the solvent has reached the solid medicament, the solid substance should be dissolved in the solvent to obtain the desired injection liquid, as shown in FIG. 6 of said European patent application 144,551. In practice this can only be accomplished by shaking the syringe. Even when the user carries out this shaking operation with the syringe in a precisely upright position, inevitably injection liquid will be spilled via the passageway in the syringe tip or via the needle. Especially when the syringe accomodates an injection liquid which includes a substance, risky or dangerous for the environment, for instance a cytostatic or a comparable substance, this is higly undesirable.

Although the above-discussed known syringe is particularly intended for solid-solvent accomodation, it is also suggested in said European patent application 144,551 to use this syringe for accomodating two liquid components in it. The known syringe, however, does not lend itself in practice for such accomodating a liquid component in front of the separating stopper, because during storage of the syringe, at least part of said liquid component will enter the interior of the syringe tip or of the needle and consequently will easily withdraw from mixing with the diluting liquid behind the separating stopper upon use. In addition, during storage of the syringe said liquid component in front of the stopper is in continuous contact with the cap closing the tip or with the injection needle, which may exert an adverse influence on the quality of this liquid component. Further the above disadvantages for the solid-solvent accomodation equally apply to the accomodation of two liquid components.

The syringe of the present invention does not show any of the above disadvantages. On the contrary, the pre-mixing operation can even be carried out amply time before use, as a making the injector ready for use operation, without exposing the injection liquid or liquids to contamination with the environment. In case a needle with a needle guard provided with a bacteria filter is used, the interior of the syringe remains completely sterile during and after said making ready for use operation. Further no injection liquid can be spilled when the liquids are mixed by shaking to obtain the desired injection liquid.

Although the syringe according to the invention is destined in particular for receiving two or more injection liquids, the use is not restricted hereto. The same syringe can also be used equally successfully to accomodate a solid medicament in the space between the sealing stopper and the separating stopper and a diluent or solvent therefor in the space behind the separating stopper. It is the merit of the invention that the syringe according to the invention provides such a great extent of flexibility that the syringe can be used without any adapting means both for accommodating two or more different injection liquids and for accommodating a solid medicament and a solvent or diluent for said medicament. Also for this application the use of a needle guard with bacteria filter offers the advantage, that during the operation of dissolving the solid medicament in the solvent the syringe remains sterile, because the needle guard does not need to be removed beforehand. The position of the sealing stopper in the ampoule, i.e.

the distance between the sealing stopper and the separating stopper, may be varied at will, provided it is ensured that the empty space remaining in front of the sealing stopper is so large that it can comprise at least the quantity of liquid behind the separating stopper.

The syringe according to the invention will usually be constructed as a two-chamber syringe, i.e. it will comprise only one separating stopper. The syringe can then be filled very simply by first providing the sealing stopper and then providing, in a vertical position, successively the first injection liquid, the separating stopper, the second injection liquid, and finally the plunger. Of course, the reverse sequence is equally possible. After providing the needle holder comprising or not comprising an injection needle, preferably covered by a needle guard, and the finger grip, the syringe is ready for delivery to the customer.

This filling possibility moreover presents a unique opportunity to accommodate without any problems a freeze-dried medicament in the front compartment and a solvent or diluent for said medicament in the rear compartment. The medicament in powder form is usually provided as such in the compartment destined for that purpose. This is objectionable because, for example due to dusting, medicament may get lost or arrive in the atmosphere; this latter disadvantage is the more prominent when toxic medicaments are used, for example, cytostatics and the like. Moreover, in the conventional manner of filling the possibility is present that a little powdered medicament may contaminate ("infect") the outside of the ampoule and/or the stoppers and even arrive - prematurely - in the solvent. In the above-described filling method of the syringe according to the invention, after positioning the sealing stopper appropriately, a medicament in a suitable formulation, for example, a concentrated solution or a paste, is provided in the front compartment destined for the medicament. Because the composition is not dry, it is not dusty, so that the above disadvantages are avoided. The medicament formulation is then lyophilized, i.e. the formulation already provided in the ampoule is freeze-dried at reduced pressure at a temperature which generally is strongly decreased. The lyophilized medicament is now sealed from the atmosphere by positioning the separating stopper, after which the solvent for the medicament and the plunger can be provided in this sequence. It is advantageous to situate the by-pass means at such a position of the wall of the ampoule that the distance between the front end of the by-pass means and the rear face of the sealing stopper is greater than the length of the column of lyophilized medicament provided in said front compartment. As a result of this it is prevented that the lyophilized medicament fills the by-pass means and in this manner may obstruct the passage for the solvent or diluent during use.

The by-pass means for the injection liquid in the shaft of the needle holder may be constructed in various manners, for example, as described in the above-mentioned U.S. Pat. No. 4,496,344. At least one slot is preferably recessed in the inner wall of the shaft of the needle holder which extends in the longitudinal direction of the shaft over a length which is slightly larger than the length of the sealing stopper and which adjoins at least one slot, radially recessed in the rear face of the neck and communicating with the rear aperture of the needle. In another preferred embodiment the inner wall of the shaft of the needle holder comprises at least one inwardly projecting ridge which extends in the longitudinal direction of the shaft over a length which is slightly larger than the length of the sealing stopper, and the front face of the sealing stopper or the rear face of the neck of the needle holder comprises a few spacing supports, so that during use of the syringe the sealing stopper is deformed by contact with the ridge or ridges, a passage being formed for the injection liquid behind the sealing stopper allowing the injection liquid to reach the injection needle past the said stopper. In this latter preferred embodiment the spacing supports, if they are provided on the rear face of the neck of the needle holder, constitute preferably one or more ridges which extend(s) radially on said rear face as a continuation of the ridge or ridges on the inner wall of the shaft. In again another preferred embodiment the inner wall of the shaft of the needle holder has a circular or oval cross-section and the front face of the sealing stopper or the rear face of the neck of the needle holder comprises a few spacing supports, the space bounded by the inner wall of the shaft and the rear face of the neck of the needle holder or the spacing supports on the said rear face, respectively, having a larger circumference than the expanded sealing stopper and being slightly longer than the sealing stopper or the sealing stopper including the spacing supports, respectively. In this way the sealing stopper, in its foremost position within the shaft of the needle holder, can fill the said space substantially entirely, but an opening remains around said stopper. In still another embodiment the by-pass means for the injection liquid in the shaft of the needle holder may be constructed as described in the non-prepublished Netherlands Patent Application 8500341 in the name of the Applicants. In this embodiment the by-pass means is constructed as a duct recessed in the side wall of the shaft and adjoining the needle holder neck on the outside of the front end wall of the shaft, an aperture being recessed in the front end of the shaft. When using the syringe, air present in front of the sealing stopper can escape through said aperture so that the injection can be administered directly without de-aerating the syringe, the so-called "piqure-directe" method.

The by-pass means in the wall of the ampoule may also be constructed in various manners. The ampoule may be made of glass or of a suitable synthetic material; in the latter case the ampoule may be manufactured, for example, by injection moulding. When the ampoule is made of synthetic material the by-pass means in the wall of the ampoule preferably consists of at least one groove recessed in the inner wall of the ampoule and extending in the longitudinal direction of the ampoule over a length which is slightly larger than the length of the separating stopper of the collective separating stoppers. In another preferred embodiment the inner wall of the ampoule at the area of the by-pass comprises at least one ridge which extends in the longitudinal direction of the ampoule over a length which is slightly larger than the length of the separating stopper or the collective separating stoppers, so that the separating stopper or stoppers, during use of the syringe, is/are deformed by contact with the ridge or ridges, a passage for the liquid behind the separating stopper of stoppers being formed through which the liquid can pass said stopper or stoppers. Such by-pass means may also be made in a glass ampoule wall, but synthetic materials are better suited for this purpose. A glass ampoule is by far to be preferred to a synthetic material ampoule because no diffusion of air oxygen to the substances accommodated in the ampoule can occur through the glass wall so that oxidative decomposition of the said substances is avoided. Moreover, synthetic materials are generally less suitable than glass to store therein for a longer period of time liquids destined for injection, because synthetic materials can contaminate the liquids or can adversely influence the stability of the said liquids. In a glass ampoule, the wall of the ampoule can most simply be provided with a by-pass means by deforming the wall of the ampoule at the area of the by-pass over a lenth which is slightly larger than the length of the separating stopper or collective separating stoppers, so that, upon use of the syringe, the liquid behind the separating stopper or stoppers can pass said stopper or stoppers at the area of the deformation. Such a deformation of the ampoule wall may be in the form as shown in the U.S. Pat. No. 2,717,601 mentioned hereinbefore. For example, the local deformation of the ampoule wall consists preferably of at least one outwardly projecting longitudinal bulge of the ampoule wall, so that upon use of the syringe, the liquid behind the separating stopper or stoppers can reach the substance in front of the separating stoppers or front separating stopper, or of at least one inwardly projecting longitudinal bulge of the ampoule wall so that, upon use of the syringe, the separating stopper or stoppers is/are deformed by contact with the inwardly projecting bulge or bulges, a passage for the liquid behind the separating stopper or stoppers being formed allowing the liquid to reach the substance in front of the separating stopper or front separating stopper past said stopper or stoppers. The ampoule wall may also be deformed locally in such way that the ampoule has an oval cross-section at that area so that, upon use of the syringe, the liquid behind the separating stopper or stoppers can reach the substance in front of the separating stopper or front separating stopper.

A local deformation of the wall of the ampoule in the form of one or more outwardly projecting longitudinal bulges is generally considered to be the best suitable solution for a by-pass means in the glass ampoule wall, because it can be very simply provided in an ampoule wall and, upon use of the syringe, forms a reliable passage for the liquid. The needle holder provided with a collar ensures, together with the finger grip, that such a bulge or such bulges in the glass ampoule wall is/are protected from damage or fracture. For example, when the syringe is dropped on a table or on the floor, it will now in most of the cases land on the needle holder collar and finger grip projecting beyond the ampoule wall, so that the bulge in the ampoule wall cannot contact the table or the floor. Moreover, packaging such syringes is easier, and during transport of the packaged syringes fractures will less easily occur due to the protecting influence of the needle holder collar and the finger grip. A syringe without a needle holder, as described in the U.S. Pat. No. 2,717,601 mentioned hereinbefore lacks such a protection of the by-pass means in the glass wall of the ampoule. It will be obvious that the invention relates more in particular to pre-fillable or pre-filled syringes, i.e. syringes which can be filled by the customer or supplier ample time before use.

The components of the syringe, such as ampoule, needle guard, finger grip and plunger rod, can be connected in the usual manner, for example, by means of a screwed joint, bayonet or snap-cap connection. The injection needle is preferably covered by a needle guard to keep the needle in a sterile condition. In case the injection needle is supplied separately, the needle holder neck is preferably constructed externally as a cone, for example, a Luer cone or Luer lock cone, around which the needle comprising a needle sleeve can be connected in a fitting manner. Usually said neck is sealingly provided with a detachable cap to keep the contents of the syringe sterile before use. Said cap is preferably also provided with a bacteria filter to keep the syringe sterile even during and after the mixing operation. Needle holder, finger grip and plunger rod are preferably manufactured from a suitable non-deformable synthetic material, the stoppers from a suitable resilient material, preferably rubber of a pharmaceutical quality.

For administering an injection it is common practice to find out whether the tip of an injection needle is present at the correct place in the patient's body, i.e. whether or not in a bloodvessel. Therefore, the plunger is usually slightly retracted by means of the plunger rod, body fluid or no body fluid, respectively, reaching the ampoule via the needle duct: the so-called nurse-aspiration. When the ampoule is manufactured from a transparent material, the user of the syringe can ascertain whether the tip of the injection needle is in a vein, if so desired, and whether hence the injection liquid will or will not be injected directly into the blood stream. During said nurse-aspiration the sealing stopper is not allowed to be retracted together with the plunger, because as a result of this the passage to the ampoule could be obstructed so that no body fluid could reach the ampoule. As a particular aspect of the invention it has now been found that said nurse-aspiration can take place without any hindrance when three conditions are satisfied, namely: (1) when the shaft of the needle holder has a slightly larger inner circumference than the inner wall of the ampoule, (2) when the rear face of the sealing stopper comprises a few recesses or spacing supports provided in or on the circumferential edge of the sealing stopper, and (3) when, in case of recesses provided in the rear face of the sealing stopper, a circumferential groove is recessed in the backmost portion of the shaft of the needle holder adjoining the ampoule. As a result of this, body fluid can be drawn into the ampoule with no hindrance during the above-described nurse-aspiration.

Since the needle holder shaft is slightly wider than the inner wall of the ampoule, the sealing stopper cannot be drawn into the ampoule during nurse-aspiration and thus obstruct the passage for body fluid. In the case of spacing supports on the circumferential edge of the rear face of the sealing stopper, the sealing stopper is slightly retracted during aspiration until the spacing supports bear against the front inner edge of the inner wall of the ampoule and prevent further retraction of the sealing stopper; body fluid can now reach the ampoule via the bypass means in the shaft and across the spacing supports. In the case of recesses in the rear face of the sealing stopper, said stopper is retracted slightly during aspiration till against the front inner edge of the ampoule; body fluid can now reach the ampoule via the by-pass means in the shaft, the circumferential groove in the shaft and the recesses in the sealing stopper. It will be obvious that this provision cannot only be used in the syringe according to the invention, but also in all syringes provided they comprise a needle holder having a shaft which comprises a by-pass means for injection liquid and which, upon use of the syringe, can accomodate the sealing stopper.

The invention will now be described in greater detail with reference to an embodiment which is shown in the drawings, in which.

Figure 1:
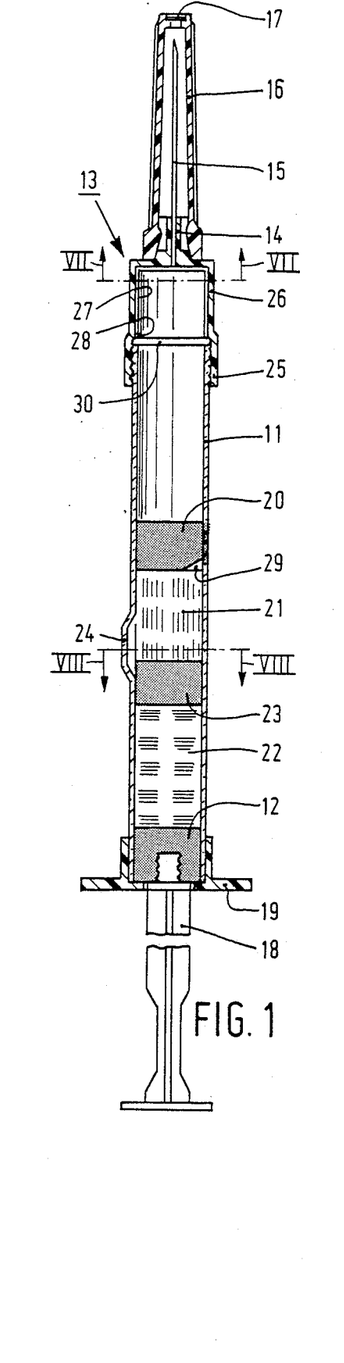
FIG. 1 is a longitudinal sectional view of a syringe according to the invention in the condition in which it can be transported and stored.

The syringe shown in FIG. 1 comprises an ampoule 11, in which at one end a plunger 12 is provided while the other end comprises a needle holder 13 in the neck 14 of which an injection needle 15 is connected. The injection needle is covered in a sterile manner by a needle guard 16 which at its front comprises an aperture with a bacteria filter 17. The plunger can be moved by means of a plunger rod 18 which is connected to the plunger, for example, by means of a screwed joint. At the same end where the plunger is present, the ampoule comprises on its outside a finger grip 19 which is connected around the ampoule according to the so-called snap-cap principle. The ampoule is preferably manufactured from glass, the finger grip preferably from a slightly resilient but non-deformable material, for example, a synthetic material. In another suitable embodiment the finger grip forms one assembly with the ampoule and may then be formed as a flange-like part of the ampoule projecting radially outwards.

Instead of a needle guard with bacteria filter, a needle guard which is closed entirely at its front end may alternatively be used. The use of a needle guard with bacteria filter is to be preferred, however, because in this case the needle can remain protected in a sterile manner for a longer period of time, namely during mixing and de-aerating. Moreover the syringe then may be stored an additional period after the mixing or making ready for use operation before it is actually used.

A sealing stopper 20 is present in the part of the ampoule remote from the plunger at a considerable distance from the open end of the ampoule. Two different liquids 21 and 22 which are kept separated from each other by a separating stopper 23 are present in the ampoule between the plunger and the stopper. The stoppers are manufactured from rubber of a pharmaceutical quality. The ampoule furthermore comprises a by-pass means for the injection liquid in the form of a longitudinal bulge 24 in the glass wall, as a result of which a longitudinal slot-shaped aperture is formed. This slot-shaped aperture terminates at its rear end near separating stopper 23, so that the injection liquids in the stored condition of the syringe cannot reach each other.

The by-pass means in the ampoule wall may also be constructed differently. For example, the glass wall may locally be bent inwards longitudinally, so that internally at the area of the passage a longitudinal ridge is formed in the ampoule. The said ridge can cause the separating stopper to be deformed upon contacting, so that on either side of the ridge passages for the liquid are formed. Of course, two or more slot-shaped apertures or ridges may also be present. The wall of the glass ampoule at the area of the by-pass may also have an oval cross-section allowing liquid to pass the stopper in the passage.

The needle holder 13 comprising a neck 14 is connected to the ampoule by means of a collar 25. A shaft 26 is present between the neck and the collar. The needle holder is preferably manufactured from a slightly resilient material which, however, has sufficient non-deformability, for example, a suitable synthetic material, and is connected to the front end of the ampoule by means of a so-called snap-cap connection. In another embodiment the needle holder may be connected to the ampoule by means of a screwed or a bayonet connection, or, when the ampoule also comprises a collar or a flange, by means of a clamping ring. Four slots 27 are recessed in the inner wall of the shaft and the rear face of the neck and the rear face of the neck and communicate with the injection needle. The collective cross-section of the slots should at least be as large as that of the duct in the injection needle. The shaft of the needle holder is constructed in such way that when the sealing stopper is moved forward axially, it is received by the shaft in a sliding manner. The inner wall of the shaft, therefore, has a slightly larger circumference than the inner wall of the ampoule; however, this circumference may not be larger than the circumference of the sealing stopper in the expanded condition. The inner wall of the shaft is slightly longer than the length of the sealing stopper so that the part 28 of the slots adjoining the ampoule is uncovered when the sealing stopper is moved in its extreme forward position to against the rear face of the neck of the needle holder. In order to be able for nurse-aspiration, the rear face of the sealing stopper comprises three notches 29 (see also FIG. 9) which are recessed in the circumferential edge of the sealing stopper, while a circumferential groove 30 which communicates with the slots 27 in the shaft of the needle holder is recessed in the part of the shaft of the needle holder adjoining the ampoule. The operation of these provisions upon nurse-aspiration has been explained already hereinbefore.

Figure 2:
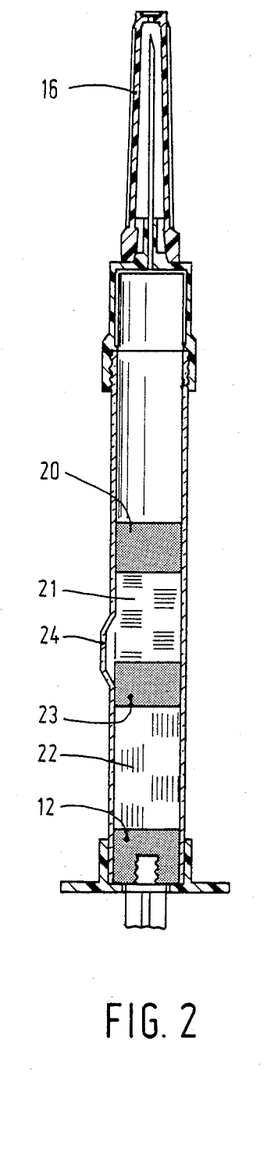
FIGS. 2, 3, 4, 5 and 6 in outline are longitudinal sectional views of the same syringe but this time during use of the syringe.

The use of the syringe according to the invention will be described with reference to FIGS. 2, 3, 4, 5 and 6. The syringe shown in these Figures corresponds in outline to the one of FIG. 1. However, details which are not so important for the explanation, for example, the provisions suitable for the nurse-aspiration, are not shown in these Figures. FIG. 2 in outline is equal to FIG. 1.

Figure 3:
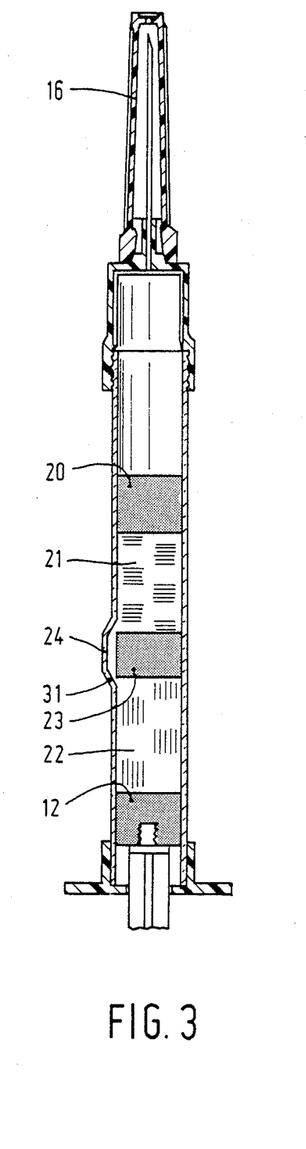
Figure 4:
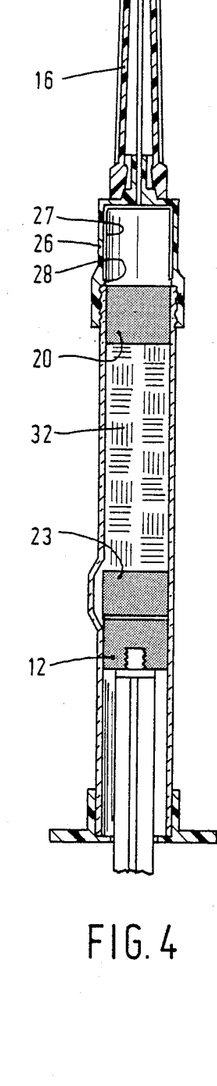
Figure 5:
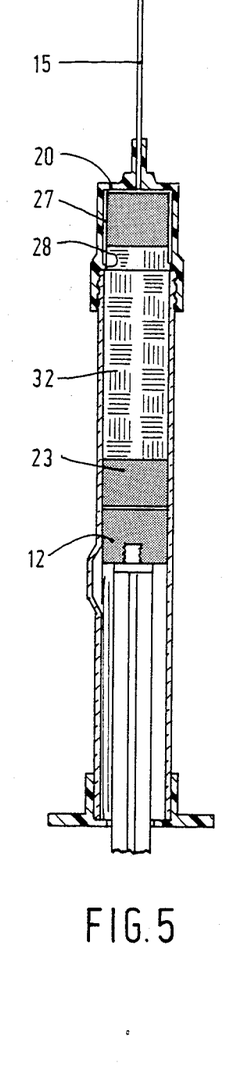
Figure 6:
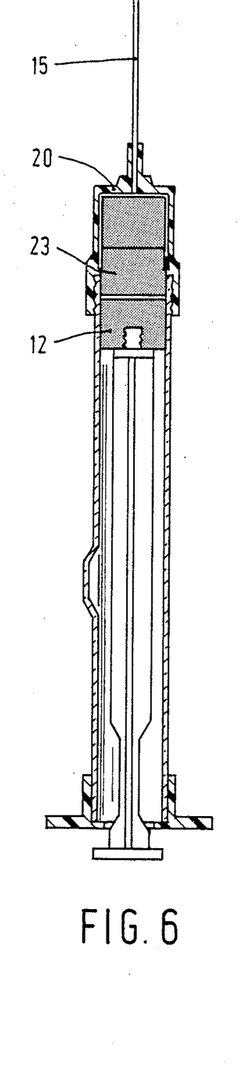
Figure 7:
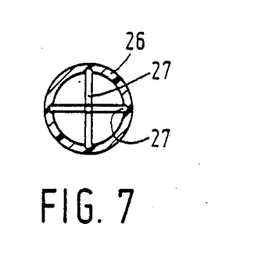
FIGS. 7 and 8 are cross-sectional views through the needle holder and ampoule respectively of the FIG. 1 syringe, taken on the lines VII—VII and VIII—VIII viewed in the direction of the needle and of the plunger, respectively.
Figure 8:
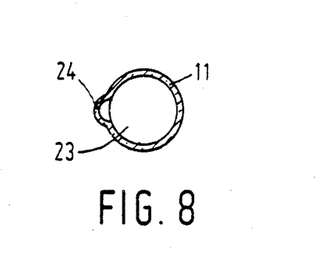

When the syringe according to the invention is used, the plunger 12 is pushed forward by means of the plunger rod. The pressure exerted on the plunger propagates via the liquid columns 22 and 21 and the stopper 23 to the stopper 20. The air in the space in front of the sealing stopper 20 can escape via the injection needle and the bacteria filter in the needle guard. When the rear face of the separating stopper 23 has been moved past the rear end 31 of the bypass means 24, as shown in FIG. 3, the liquid 22 can pass the separating stopper and can reach the liquid 21. When the plunger 12 is further pushed forward, liquid 22 is added completely to liquid 21, the sealing stopper 20 being moved forward in the ampoule. This is completed when the front face of the plunger 12 engages the rear face of the separating stopper 23, as is shown in FIG. 4. After shaking the syringe, so that the liquids are mixed, the injection liquid 32 is ready to be injected, the sealing stopper 20 being in the front end of the ampoule. By exerting further pressure on the plunger, the sealing stopper 20 is moved into the shaft 26 of the needle holder. When the stopper has been moved into the shaft until the rear face has passed the part 28 of the slots adjoining the ampoule, as is shown in FIG. 5, the injection liquid 32 present behind the sealing stopper can pass said stopper, after deaerating if so desired, via the slots 27 recessed in the inner wall of the shaft and thus reach the injection needle 15. After removal of the needle guard 16, the injection liquid can be injected into a patient. When the provisions shown in FIG. 1 are used, nurse-aspiration may be carried out, if desired, the notches 29 recessed in the circumferential edge of the rear face of the sealing stopper 20 ensuring that the admission of body fluid to the ampoule cannot be obstructed when during said nurse-aspiration the sealing stopper is slightly retracted into the shaft of the needle holder. Under the influence of the forward movement of the plunger, the injection liquid 32 can now be expelled as completely as possible until the condition shown in FIG. 6 is reached in which the plunger and the stoppers engage each other; the front face of the sealing stopper 20 engages the rear face of the neck of the needle holder and the plunger and stoppers are in their extreme forward position.

Figure 9:
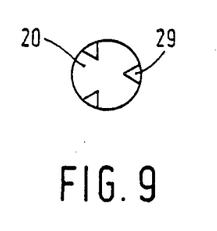
FIG. 9 is a bottom view of the sealing stopper of the FIG. 1 syringe, viewed in the direction of the injection needle.
Figure 10:
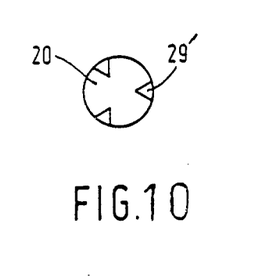
FIG. 10 is a bottom view of another embodiment of the sealing stopper, viewed in the direction of the injection needle.

FIG. 10 shows sealing stopper 20 with a plurality of spacing supports 29' on the circumferential edge of stopper 20, wherein supports 29' project downwardly from the bottom of stopper 20 in contrast to recesses 29 in FIG. 9 which are notched into the bottom surface of stopper 20.

It will be feasible that the front face of the plunger and the rear face of the separating stopper, as well as the front face of the separating stopper and the rear face of the sealing stopper, are as complementary as possible and are preferably substantially flat surfaces, so as to keep the residual volume of injection liquids as small as possible. For the same reason, the front face of the sealing stopper and the rear face of the neck of the needle holder are shaped in such way that in the sealing stopper's extreme forward position the space between the front face of the stopper and the entrance to the neck aperture is as small as possible.

I claim:

1. A multi-compartment syringe for separate storage of at least two different substances to be prevented from being in contact with each other except for a period of time immediately prior to use, one of said substances being disposed at a foremost position in said syringe, said syringe comprising:
   a hollow substantially cylindrical ampoule which is open at both ends,
   a plunger to which a plunger rod is connected and which is movable in the ampoule from an initial position at one end of the ampoule toward another end thereof and seals said ampoule,
   a sealing stopper having dimensions such that the sealing stopper can be provided in a sealing manner in said ampoule and so as to be movable in the ampoule in order to be able to separate the substance disposed at said foremost position in the ampoule from a front end of the ampoule,
   at least one rotationally symmetrical separating stopper means provided in the ampoule between said plunger and said sealing stopper and being movable therein, the circumference of said separating stopper means before use of the syringe adjoining the inner wall of the ampoule in a sealing manner and keeping the different substances present in the ampoule separated from each other, and
   a needle holder comprising:
   (a) a collar connected to the front end of the ampoule in a sealing manner,
   (b) a neck having an injection needle sealably attached thereto and covered by a needle guard to keep the needle in a sterile condition, said needle guard comprising a bacteria filter,
   (c) a hollow, substantially cylindrical shaft disposed between said collar and said neck, the shaft being proportioned so that the space bounded by the inner wall of the shaft and the rear face of the neck has one of (i) substantially the same circumference as and (ii) a slightly larger circumference than the inner wall of the ampoule and is at least longer than the sealing stopper, and
   (d) a needle holder by-pass means in the inner wall of the shaft through which injection liquid behind the sealing stopper can reach the injection needle when, during use of the syringe, the sealing stopper is moved forward into the shaft of the needle holder, said syringe being characterized in that an ampoule by-pass means is formed in the wall of the ampoule, which by-pass means has a length at least as great as that of the separating stopper means, and through which by-pass means, during use of the syringe, liquid behind the separating stopper means can reach the substance in front of the separating stopper means and can mix with said substance or can dissolve it, but which by-pass means, before use of the syringe, is sealed from the liquid present behind said separating stopper means by means of the separating stopper means, and the ampoule, before use of the syringe, comprises an empty space which is not filled with substance and which is bounded on the rear and lateral sides by the front face of the sealing stopper and the inner wall of the ampoule, and which on its front is in open communication with the space in the shaft of the needle holder, said empty space in the ampoule being at least as long as the distance from the front face of the plunger when said plunger is in its initial position at said one end of the ampoule to the rear end of said ampoule by-pass means.

2. A syringe as claimed in claim 1, characterized in that at least one slot is recessed in the inner wall of the shaft of the needle holder which extends in the longitudinal direction of the shaft over a length which is slightly larger than the length of the sealing stopper and which adjoins at least one slot, radially recessed in the rear face of the neck and communicating with the rear aperture of the needle.

3. A syringe as claimed in claim 1 characterized in that the inner wall of the shaft of the needle holder comprises at least one inwardly projecting ridge which extends in the longitudinal direction of the shaft over a length which is slightly larger than the length of the sealing stopper, and that the front face of the sealing stopper or the rear face of the neck of the needle holder comprises a few spacing supports so that, upon use of the syringe, the sealing stopper is deformed by contact with the ridge or ridges, a passage for the injection liquid behind the sealing stopper being formed allowing the injection liquid to reach the injection needle past said stopper.

4. A syringe as claimed in claim 3, wherein the spacing supports are provided on the rear face of the neck of the needle holder, and the spacing supports constitute at least one ridge which extends radially of said rear face as a continuation of the said ridge on the inner wall of the shaft.

5. A syringe as claimed in claim 1, characterized in that the inner wall of the shaft of the needle holder has a circular or oval cross-section, that the front face of the sealing stopper or the rear face of the neck of the needle holder comprises a few spacing supports, and that the space bounded by the inner wall of the shaft and the rear face of the neck of the needle holder or the spacing supports on said rear face, respectively, has a larger circumference that the expanded sealing stopper and is slightly longer than the sealing stopper or the sealing stopper including the spacing supports, respectively, so that the sealing stopper in its foremost position can substantially entirely fill said space, but an opening remains around said stopper.

6. A syringe as claimed in claim 1, characterized in that the ampoule by-pass means comprises at least one groove recessed in the inner wall of the ampoule and extending in the longitudinal direction of the ampoule over a length which is slightly larger than the length of the separating stopper or the collective separating stoppers.

7. A syringe as claimed in claim 1, characterized in that the inner wall of the ampoule at the area of the by-pass comprises at least one ridge which extends in the longitudinal direction of the ampoule over a length which is slightly larger than the length of the separating stopper or the collective separating stoppers, so that, when using the syringe, the separating stopper or stoppers is/are deformed by contact with the ridge or ridges, a passage for the liquid behind the separating stopper or stoppers being formed through which the liquid can pass said stopper or stoppers.

8. A syringe as claimed in claim 1, characterized in that at the area of the ampoule by-pass means the wall of the ampoule is deformed over a length which is slightly larger than the length of the separating stopper or the collective separating stoppers so that, when using the syringe, the liquid behind the separating stopper or stoppers can pass said stopper or stoppers at the area of the deformation.

9. A syringe as claimed in claim 1, in which a lyophilized medicament is accommodated in the front compartment of the syringe, bounded by the sealing stopper, the inner wall of the ampoule and the separating stopper or front separating stopper, and a solvent or diluent for said medicament is accommodated in the compartment behind said separating stopper or front separating stopper, characterized in that said ampoule by-pass means is situated at such a position of the wall of the ampoule that the distance between the front end of said by-pass means and the rear face of the sealing stopper is greater than the length of the column of lyophylized medicament provided in said front compartment.

10. A syringe as claimed in claim 1, in which the shaft of the needle holder has a slightly larger circumference than the inner wall of the ampoule, characterized in that the rear face of the sealing stopper comprises a plurality of recesses which are provided in the circumferential edge of the sealing stopper, and in that a circumferential groove is recessed in the backmost portion of the shaft of the needle holder adjoining the ampoule.

11. A syringe, comprising:

a hollow, substantially cylindrical ampoule which is open at both ends, a plunger which is movable in the ampoule and seals said ampoule and to which a plunger rod is connectable, a substantially rotationally symmetrical sealing stopper having dimensions such that the sealing stopper can be provided in a sealing manner in said ampoule and so as to be movable in the ampoule, and a needle holder comprising:

(a) a collar connected to the front end of the ampoule in a sealing manner, (b) a neck for sealingly attaching an injection needle, covered by a needle guard to keep the needle in a sterile condition, (c) a hollow, substantially cylindrical shaft disposed between the collar and the neck, the shaft being proportioned so that the space bounded by the inner wall of the shaft and the rear face of the neck has one of (i) substantially the same circumference as and (ii) a slightly larger circumference than the inner wall of the ampoule and is at least longer than the sealing stopper, and (d) a needle holder by-pass means in the inner wall of the shaft through which injection liquid behind the sealing stopper can reach the injection needle when, upon using the syringe, the sealing stopper is moved forward into the shaft of the needle holder, said syringe being characterized in that the rear face of the sealing stopper comprises a plurality of recesses which are provided in the circumferential edge of the sealing stopper, and in that a circumferential groove is recessed in the backmost portion of the shaft of the needle holder adjoining the ampoule.

12. A syringe, comprising:

a hollow, substantially cylindrical ampoule which is open at both ends, a plunger which is movable in the ampoule and seals said ampoule and to which a plunger rod is connectable, a substantially rotationally symmetrical sealing stopper having dimensions such that the sealing stopper can be provided in a sealing manner in said ampoule and so as to be movable in the ampoule, and a needle holder comprising:

(a) a collar connected to the front end of the ampoule in a sealing manner, (b) a neck for sealingly attaching an injection needle, covered by a needle guard to keep the needle in a sterile condition, (c) a hollow, substantially cylindrical shaft disposed between the collar and the neck, the shaft being proportioned so that the space bounded by the inner wall of the shaft and the rear face of the neck has one of (i) substantially the same circumference as and (ii) a slightly larger circumference than the inner wall of the ampoule and is at least longer than the sealing stopper, and (d) a needle holder by-pass means in the inner wall of the shaft through which injection liquid behind the sealing stopper can reach the injection needle when, upon using the syringe, the sealing stopper is moved forward into the shaft of the needle holder, said syringe being characterized in that the rear face of the sealing stopper comprises a plurality of spacing supports which are provided on the circumferential edge of the sealing stopper.

13. A syringe, comprising:
a hollow, substantially cylindrical ampoule which is open at both ends,
a plunger which is movable in the ampoule and seals said ampoule and to which a plunger rod is connectable,
a substantially rotationally symmetrical sealing stopper having dimensions such that the sealing stopper can be provided in a sealing manner in said ampoule and so as to be movable in the ampoule,
at least one separating stopper disposed in the ampoule in a sealing manner so as to keep at least two different substances separated from each other prior to use of the syringe, and
a needle holder comprising:
(a) a collar connected to the front end of the ampoule in a sealing manner,
(b) a neck for sealingly attaching an injection needle, covered by a needle guard to keep the needle in a sterile condition,
(c) a hollow, substantially cylindrical shaft disposed between the collar and the neck, the shaft being proportioned so that the space bounded by the inner wall of the shaft and the rear face of the neck has one of (i) substantially the same circumference as and (ii) a slightly larger circumference than the inner wall of the ampoule and is at least longer than the sealing stopper, and
(d) a needle holder by-pass means in the inner wall of the shaft through which injection liquid behind the sealing stopper can reach the injection needle when, upon using the syringe, the sealing stopper is moved forward into the shaft of the needle holder,
said syringe being characterized in that the rear face of the sealing stopper comprises a plurality of recesses which are provided in the circumferential edge of the sealing stopper, and in that a circumferential groove is recessed in the backmost portion of the shaft of the needle holder adjoining the ampoule.

14. A syringe, comprising:
a hollow, substantially cylindrical ampoule which is open at both ends,
a plunger which is movable in the ampoule and seals said ampoule and to which a plunger rod is connectable,
a substantially rotationally symmetrical sealing stopper having dimensions such that the sealing stopper can be provided in a sealing manner in said ampoule and so as to be movable in the ampoule,
at least one separating stopper disposed in the ampoule in a sealing manner so as to keep at least two different substances separated from each other prior to use of the syringe, and
a needle holder comprising:
(a) a collar connected to the front end of the ampoule in a sealing manner,
(b) a neck for sealingly attaching an injection needle, covered by a needle guard to keep the needle in a sterile condition,
(c) a hollow, substantially cylindrical shaft disposed between the collar and the neck, the shaft being proportioned so that the space bounded by the inner wall of the shaft and the rear face of the neck has one of (i) substantially the same circumference as and (ii) a slightly larger circumference than the inner wall of the ampoule and is at least longer than the sealing stopper, and
(d) a needle holder by-pass means in the inner wall of the shaft through which injection liquid behind the sealing stopper can reach the injection needle when, upon using the syringe, the sealing stopper is moved forward into the shaft of the needle holder,
said syringe being characterized in that the rear face of the sealing stopper comprises a plurality of spacing supports which are provided on the circumferential edge of the sealing stopper.

* * * * *